United States Patent [19]

Barrish et al.

[11] Patent Number: 5,276,026

[45] Date of Patent: Jan. 4, 1994

[54] TETRAHYDROETHANONAPHTHALENEAMINE DERIVATIVES

[75] Inventors: Joel C. Barrish, Holland; Steven H. Spergel, Bensalem, both of Pa.

[73] Assignee: E. R. Squibb & Sons, Inc., Princeton, N.J.

[21] Appl. No.: 6,865

[22] Filed: Jan. 21, 1993

Related U.S. Application Data

[62] Division of Ser. No. 560,518, Jul. 31, 1990, Pat. No. 5,202,486.

[51] Int. Cl.$^5$ .................. A61K 31/55; A61K 31/445; C07D 223/02; C07D 209/54
[52] U.S. Cl. ..................... 514/212; 514/231.2; 514/278; 514/359; 540/543; 544/111; 546/17; 548/411; 548/950; 548/954
[58] Field of Search ............ 540/543; 544/111; 546/17; 548/411, 950, 954; 514/212, 231.2, 278, 359

[56] References Cited

U.S. PATENT DOCUMENTS 3,932,512  1/1976  Bharucha et al. ............. 564/427
4,680,310  7/1987  Hengartner et al. ........... 514/539

Primary Examiner—Mukund J. Shah
Assistant Examiner—Y. N. Gupta
Attorney, Agent, or Firm—Theodore R. Furman, Jr.; Suzanne E. Babajko

[57] ABSTRACT

Tetrahydronaphthaleneamine derivatives having the formula

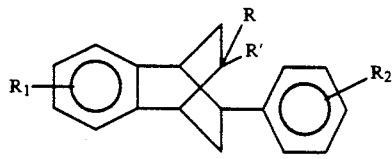

wherein R, R', $R_1$ and $R_2$ are as defined herein, are novel calcium channel blockers.

5 Claims, No Drawings

TETRAHYDROETHANONAPHTHALENEAMINE DERIVATIVES

This is a division of application Ser. No. 07/560,518, filed on Jul. 31, 1990, now U.S. Pat. No. 5,202,486.

SUMMARY OF THE INVENTION

In accordance with the present invention novel compounds having calcium channel blocking activity, useful for example as cardiovascular agents, are disclosed. The present compounds have the general formula

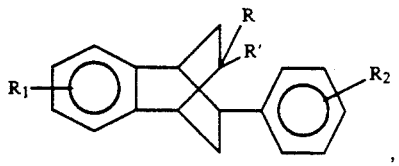

including pharmaceutically acceptable salts thereof, wherein
one of R and R' is hydrogen and the other is

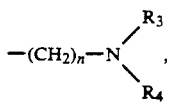

or R and R' taken together with the carbon atom to which they are attached form a 3- to 7-membered nitrogen-containing ring

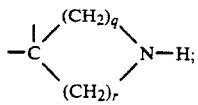

$R_1$ is hydrogen, halogen, alkyl, haloalkyl, cyano, hydroxy, alkoxy, aryl, arylalkoxy, arylalkyl, fluorosubstituted alkyl;

$R_2$ is hydrogen, halogen, alkyl, alkoxy, aryloxy, arylalkoxy, arylalkyl, cyano, hydroxy, alkanoyloxy,

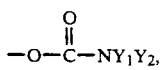

fluoro substituted alkoxy, fluoro substituted alkyl, (cycloalkyl)alkoxy, $-NO_2$, $-NY_3Y_4$, $-S(O)_m$aryl,

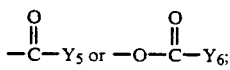

n is 0, 1, 2 or 3;
m is 0, 1 or 2;
q and r are independently 0, 1, 2, or 3, with the proviso that one of q and r must be other than zero;
$R_3$ and $R_4$ are each independently hydrogen, alkyl, cycloalkyl or arylalkyl or $R_3$ and $R_4$ together with the nitrogen atom to which they are attached are pyrrolidinyl, piperidinyl, azetidinyl or morpholinyl;
$Y_1$ and $Y_2$ are each independently hydrogen, alkyl, aryl or heteroaryl, or $Y_1$ and $Y_2$ together with the nitrogen atom to which they are attached are pyrrolidinyl, piperidinyl or morpholinyl;

$Y_3$ and $Y_4$ are each independently hydrogen, alkyl, alkanoyl, arylcarbonyl, heteroarylcarbonyl,

$Y_5$ is hydroxy, alkoxy, aryloxy, amino, alkylamino or dialkylamino: and,
$Y_6$ is alkyl, alkoxy or aryloxy.

DETAILED DESCRIPTION OF THE INVENTION

Listed below are definitions of various terms used to describe the tetrahydronaphthalene amines of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "alkenyl" refers to both straight and branched chain groups. Those groups having 2 to 10 carbon atoms are preferred.

The term "aryl" refers to phenyl and substituted phenyl. Exemplary substituted phenyl groups are phenyl groups substituted with 1, 2 or 3 amino ($-NH_2$), alkylamino, dialkylamino, nitro, halogen, hydroxyl, trifluoromethyl, alkyl (of 1 to 4 carbon atoms), alkoxy (of 1 to 4 carbon atoms), alkylthio (of 1 to 4 carbon atoms), alkanoyloxy, carbonyl, or carboxyl groups.

The term "alkanoyl" refers to groups having the formula

Those alkanoyl groups having 2 to 11 carbon atoms are preferred.

The term "heteroaryl" refers to an aromatic heterocyclic group having at least one heteroatom in the ring. Preferred groups are pyridinyl, pyrrolyl, imidazolyl, furyl, thienyl, oxazolyl or thiazolyl.

The term "cycloalkyl" refers to groups having 3, 4, 5, 6 or 7 carbon atoms.

The term "halogen" refers to fluorine, chlorine, bromine and iodine.

The terms "fluoro substituted alkyl" and "fluoro substituted alkoxy" refer to alkyl and alkoxy groups (as described above) in which one or more hydrogens have been replaced by fluorine atoms. Exemplary groups are trifluoromethyl, 2,2,2-trifluoroethyl, pentafluoroethyl, fluoromethoxy, difluoromethoxy, etc.

The compounds of formula I form acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Any other salt may then be formed from the free base and the appropriate inorganic or organic acid. Illustrative are the hydrohalides, especially the hydrochloride and hydrobromide, sulfate, nitrate, phosphate, borate, acetate, tartrate, maleate, citrate, succinate, benzoate, ascorbate, salicylate, methanesulfonate, benzenesulfonate, toluenesulfonate and the like.

The compounds of formula I, and the pharmaceutically acceptable salts thereof, are cardiovascular agents. They act as calcium entry blocking vasodilators and are especially useful as anti-hypertensive agents. Thus, by the administration of a composition containing one (or a combination) of the compounds of this invention, the blood pressure of a hypertensive mammalian (e.g., human) host is reduced. A single dose, or two to four divided daily doses, provided on a basis of about 0.1 to 100 milligrams per kilogram of body weight per day, preferably from about 1 to about 50 milligrams per kilogram per day, is appropriate to reduce blood pressure. The substance is preferably administered orally, but parenteral routes such as the subcutaneous, intramuscular, intravenous, intranasal and transdermal routes can also be employed.

As a result of the calcium entry blocking activity of the compounds of formula I, and the pharmaceutically acceptable salts thereof, these compounds, in addition to being anti-hypertensive agents, are also useful as anti-arrhythmic agents, anti-anginal agents, anti-fibrillatory agents, anti-asthmatic agents, anti-ischemic: agents, as an agent to increase the ratio of HDL-cholesterol to total serum cholesterol in the blood and in limiting myocardial infarction.

Additionally, the compounds of this invention are useful as therapy for congestive heart failure, therapy for peripheral vascular disease (e.g., Raynaud's disease), as anti-thrombotic agents, as anti-atherosclerotic agents, for treatment of cardiac hypertrophy (e.g., hypertrophic cardiomyopathy), for treatment of pulmonary hypertension, as an additive to cardioplegic solutions for cardiopulmonary bypasses and as an adjunct to thrombolytic therapy.

Compounds of this invention are also expected to be useful in the treatment of central nervous system vascular disorders, for example, as anti-stroke agents, anti-migraine agents, therapy for cerebral ischemia and therapy for subarachnoid hemorrhage, as well as in the treatment of central nervous system behavorial disorders, for example, in the treatment of psychiatric conditions including depression, mania, anxiety and schizophrenia, or for epilepsy or congition benefit.

Further, compounds of this invention are expected to be used as anti-diarrheal agents, as therapy for dysmenorrhea, as therapy for tinnitus and other auditory and vestibulatory disorders, for the alleviation of the various forms of oedema, for reversal of adriamycin resistance, regulation of cell growth, for treatment of glaucoma, renal failure, hepatoxicity (e.g., liver cirrhosis), various endocrine hypersecretory states (e.g., diabetes, pheochromocytoma), drug-induced tardive diskenesia, allergies, muscular dystrophy and cancer.

The compounds of this invention can also be formulated in combination with a beta-adrenergic agent, or antiarrhythmic agent, a diuretic such as, chlorothiazide, hydrochlorothiazide, flume-thiazide, hydroflumethiazide, bendroflumethiazide, methylchlothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories). Such combination products if formulated as a fixed dose employ the compounds of this invention within the dose range described above and the other pharmaceutically active agent within its approved dose range.

The compounds of formula I can be formulated for use in the reduction of blood pressure in compositions such as tablets, capsules or elixirs for oral administration, or in sterile solutions or suspensions for parenteral administration. The compounds of formula I may also be administered via transdermal patch or nasal inhalation solutions. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

To prepare the compounds of formula I where R is hydrogen, R' is

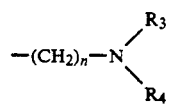

and n = 0, a naphthol of the formula

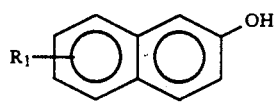

II is reacted with a compound of the formula

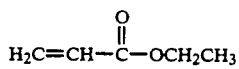

III in the presence of a free radical inhibitor, such as 2-hydroxy-4-phenyl phenol, to provide a compound of the formula

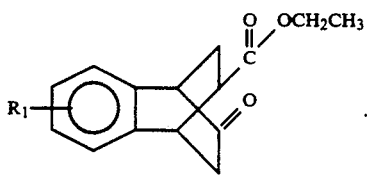

IV

Compound IV in a solvent, such as benzene, can be reacted with ethylene glycol and thereafter treated with p-toluenesulfonic acid to provide a compound of the formula

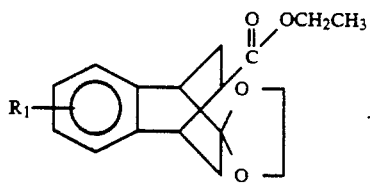

IV

Compound V can thereafter be treated in a solvent, such as methanol, with a base, such as aqueous sodium hydroxide followed by treatment with aqueous oxalic acid to provide compounds of the formula

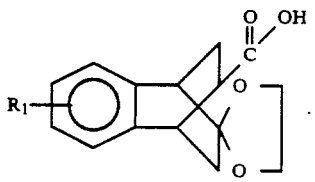

VI

Compound VI is treated first with an organic base, such as triethylamine, in a solvent such as hexane, then with an azide, e.g. diphenylphosphorylazide and thereafter reacted with benzyl alcohol to provide

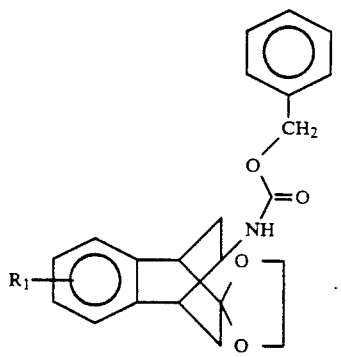

VII

Compound VII can be treated with a base, such as potassium hydride in a solvent, such as tetrahydrofuran, and thereafter reacted with a compound of the formula R$_3$-Halo,    VIII where halo is selected from Br, Cl, I, to provide compounds of the formula

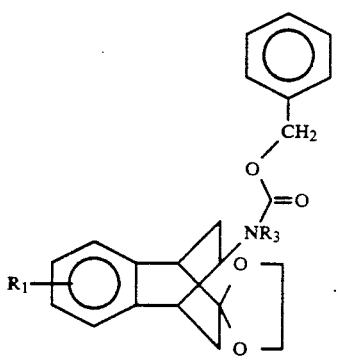

IX

Treatment of compound IX in a solvent, such as tetrahydrofuran, with hydrochloric acid provides a compound of the formula

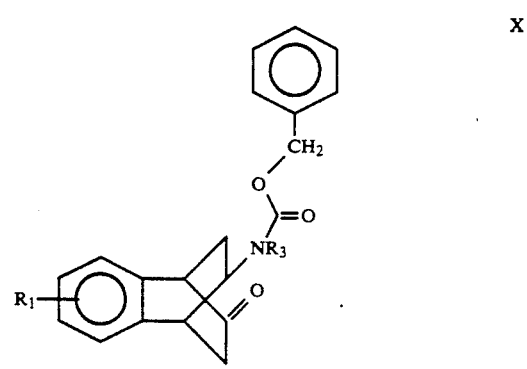

X

Reaction of Compound X in a solvent, such as tetrahydrofuran, with a compound of the formula

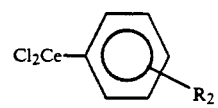

provides a diastereomeric mixture of compounds having the formula

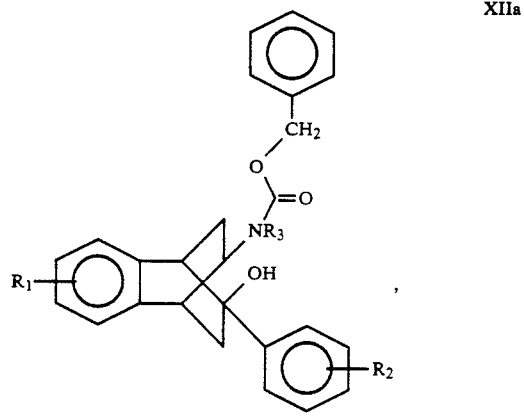

XIIa and

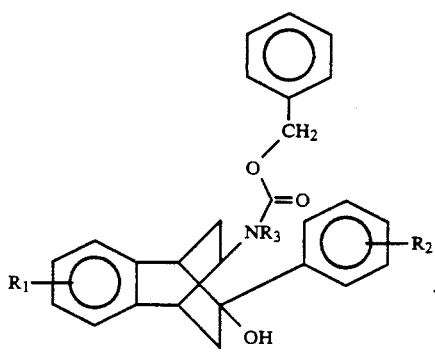

XIIb

The mixture of compounds XIIa and XIIb can be treated in a solvent, such as methylene chloride, with a reducing agent, such as triethylsilane, followed by treatment with a Lewis acid, such as borontrifluoride etherate to provide a compound of the formula

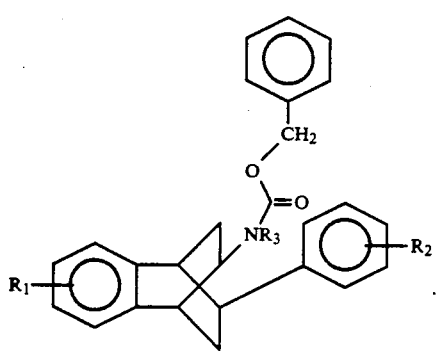 XIII

Reduction, for example by treatment with hydrogen gas in the presence of a palladium-carbon catalyst provides compounds of the formula

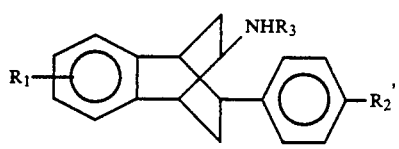 XIV that is, compounds of formula I where R is hydrogen, R' is —(CH$_2$)$_n$—NHR$_3$ and n=0.

Compounds where R' is —(CH$_2$)$_n$—NR$_3$R$_4$, n=0 and R$_4$ is other than hydrogen can be prepared from products of formula XIV by known methodology. For example, compounds of formula XIV can be subjected to reductive amination with formaldehyde or a compound of the formula R$_4$CHO (where R$_4$ is other than H) in the presence of hydrogen and a palladium on carbon catalyst or in the presence of a reducing agent, e.g., sodium borohydride.

To prepare compounds of formula I where R' is

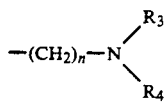

and n=1, a compound of formula V in a solvent such as toluene, and in the presence of a trialkyl aluminum reagent, e.g. trimethyl aluminum, is reacted with a compound of the formula

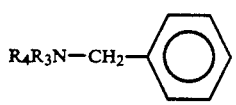 XV (where one or both of R$_3$ and R$_4$ are hydrogen and where

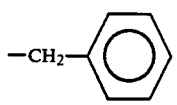

may be replaced by a different nitrogen protecting group) to provide a compound of the formula

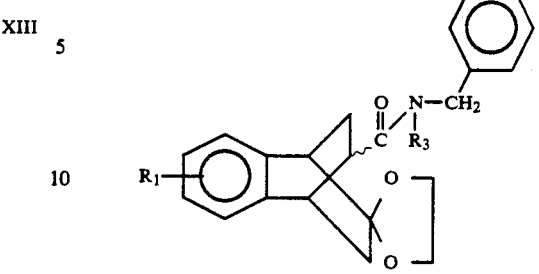 XVI which, upon treatment in a solvent, e.g. ether, with a reducing agent, e.g. lithium aluminum hydride, provides a compound of the formula

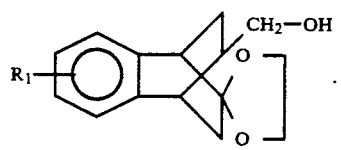 XVII

Compound XVII can thereafter be reacted as compounds IX through XIV above to provide compounds of formula I wherein n=1.

Alternatively, compounds where R' is

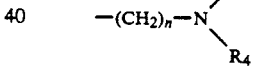

and n=1 can be prepared by reducing the ester of formula V, for example, with lithium aluminum hydride, to provide an alcohol of the formula

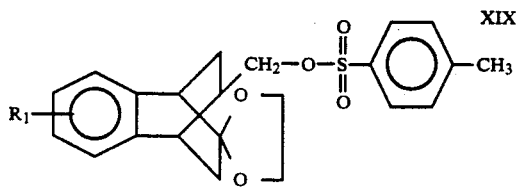 XVIII

Reaction of intermediate XVIII with p-toluenesulfonyl chloride provides the compound

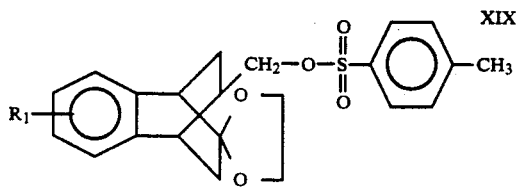 XIX which can be reacted with a cyanide (e.g., sodium cyanide) to provide a compound of the formula

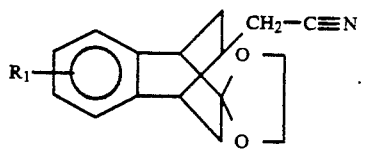  XX

Reduction of compound XX, for example with lithium aluminum hydride provides the primary amine

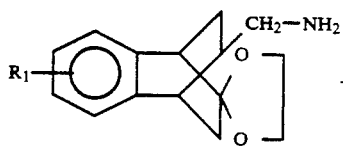  XXI (i.e., intermediates where $R_3=R_4=H$) which can be mono- or dialkylated by known techniques as those described above. Compounds of formula XXI (or the mono- or dialkylated versions thereof) can be converted to products of formula I by the methodology described above.

To prepare compounds of formula I where R' is

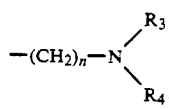

and $n=2$, the nitrile of formula XX can be reduced with diisobutylaluminum hydride to provide an aldehyde of the formula

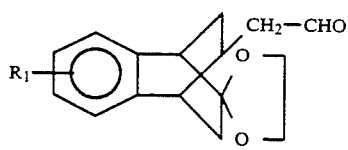  XXII which upon reductive amination with $HNR_3R_4$ in the presence of hydrogen gas and a palladium on carbon catalyst provides

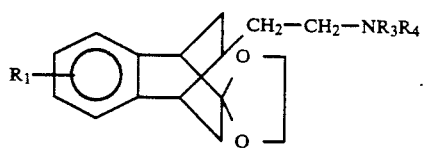  XXIII

Intermediate XXIII can thereafter be transformed to final products using the methodologies described above.

To prepare the compounds of formula I where R and R' taken together with the carbon atom to which they are attached form a 5-membered, nitrogen-containing ring, a compound of formula V in a solvent such as tetrahydrofuran can be treated with a base, such as lithium diisopropyl amide, followed by reaction with, for example, allyl bromide to provide a diastereomeric mixture of compounds of the formula

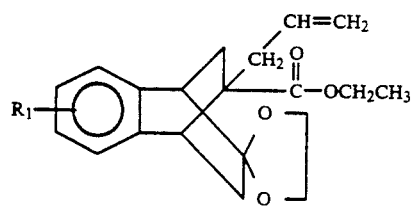  XXIVa and

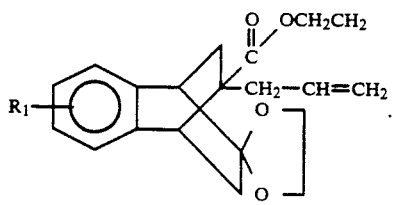  XXIVb

Compound XXIVb, in a solvent such as methanol, is then treated with ozone/oxygen mixture in the presence of a base, e.g., sodium bicarbonate, followed by treatment with dimethyl sulfide to provide

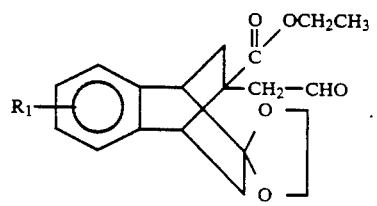  XXV

Compound XXV in a solvent, e.g. methanol, can be reacted with benzyl amine in methanolic hydrochloric acid, in the presence of a reducing agent, e.g. sodium cyanoborohydride, and molecular sieves to provide a compound of the formula

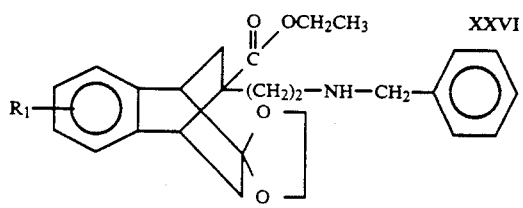  XXVI which can thereafter be treated, in a solvent, e.g. methanol, with a base, such as sodium methoxide, to give a compound of the formula

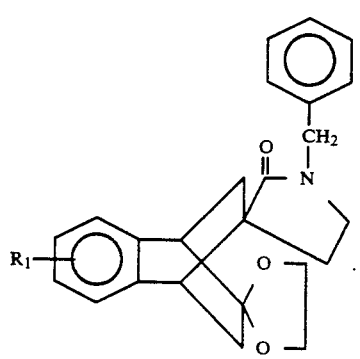  XXVII

Compound XXVII, in a solvent, e.g. tetrahydrofuran, is thereafter treated with a reducing agent, e.g. lithium aluminum hydride to provide the compound

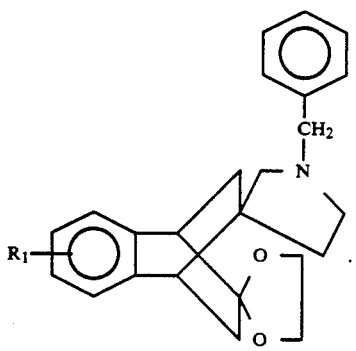

XXVIII

Compound XXVIII can thereafter be reacted as compounds IX through XIV above to provide the corresponding products of formula I where q=1 and r=2.

Treating compounds of formula V with a base followed by reaction with an allylic halide of the formula X—(CH$_2$)$_s$—CH=CH$_2$   XXIX (where s=1-3 and X is Br, I, Cl)
provides intermediates corresponding to XXIVa and b which intermediates can be treated as compounds XXIVa and b to provide corresponding compounds of formula I where r=2, 3 or 4 and q=1. Using the methodology described above and starting with an aldehyde of formula XXII, corresponding compounds where q is 2 or 3 can be prepared.

Preferred compounds of the present invention are those wherein
R is hydrogen;
R' is

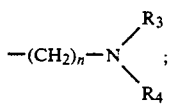

R$_1$ is hydrogen;
R$_2$ is alkoxy;
R$_3$ is hydrogen;
R$_4$ is alkyl; and
n is 0, 1.
Most preferred compounds are those wherein
R is hydrogen;
R' is

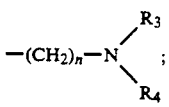

R$_1$ is hydrogen;
R$_2$ is methoxy;
R$_3$ is hydrogen;
R$_4$ is methyl;
n is 1.

The present invention will be further described by the following examples.

EXAMPLE 1

(1R*,2S*,4S*,9S*)-1,2,3,4-Tetrahydro-9-(4-methoxyphenyl)-N-methyl-1,4-ethanonaphthalen-2-amine, monohydrochloride

A.
(1R*,2S*,4S*)-9-Oxo-1,2,3,4-tetrahydro-1,4-ethanonaphthalene-2-carboxylic acid ethyl ester A mixture of β-naphthol (33 g, 228.9 mmol), ethyl acrylate (48 ml, 442.8 mmol) and 2-hydroxy-4-phenyl phenol (0.1 g) as an inhibitor were placed in a resealable bottle and heated at 175°-180° for 4 days. After cooling to room temperature, the reaction mixtures from two separate reactions were combined and the excess ethyl acrylate removed in vacuo in the hood. The resulting residue was dissolved in 500 ml of ethyl ether and poured into a 2 L separatory funnel along with 500 ml of hexanes. The mixture was washed with 2N sodium hydroxide (2×500 ml) and water (2×500 ml) (any emulsion which forms is filtered through a celite pad on a C-porosity glass frit and the cake washed with 500 ml of 1:1 ethyl ether/hexanes). The combined organic extracts were dried over anhydrous magnesium sulfate and evaporated to give a yellow residue (15 g) which contained some ethyl acrylate polymer. Kugelrohr distillation (175°-220°; 3 mm) then gave 12.78 g of an oil. The resulting exo and endo isomers could be separated by flash chromatography (100 mm×20"; 4:1 hexane:ethyl acetate) to give 3.445 g of the exo isomer, 5.975 g of the title A compound (endo) as well as 4.64 g of mixed fractions which could be rechromatographed. R$_f$ 0.31 (3:1 hexane:ethyl acetate).

B.
(1R*,2S*,4S*)-9,9-[Ethylenebis(oxy)]-1,2,3,4-tetrahydro-1,4-ethanonaphthalene-2-carboxylic acid ethyl ester To the title A compound (4.58 g, 18.74 mmol), dissolved in benzene (300 ml), was added ethylene glycol (60 ml, 1.075 mol) followed by p-toluenesulfonic acid (0.29 g) and the mixture stirred at reflux with azeotropic removal of water for 30 hours. After cooling to room temperature, the reaction mixture was poured into a separatory funnel and the organic layer washed with saturated aqueous sodium hydrogen carbonate (200 ml) and water (200 ml). The organic layer was dried over anhydrous magnesium sulfate and evaporated to give a crude residue which was purified by flash chromatography (50 mm×8"; 4:1 hexanes:ethyl acetate) to give 4.305 g of the title B compound as a slightly impure oil which solidified on storage in the refrigerator. R$_f$ 0.23 (3:1 hexane:ethyl acetate).

C.
(1R*,2S*,4S*)-9,9-[Ethylenebis(oxy)]-1,2,3,4-tetrahydro-1,4-ethanonaphthalene-2-carboxylic acid To a solution of the title B compound (5.46 g, 18.89 mmol) dissolved in methanol (45 ml) at room temperature was added a solution of sodium hydroxide (1.13 g, 28.83 mmol) dissolved in water (22 ml). The resulting pink solution was stirred at room temperature for 30 minutes and at 60° for 30 minutes. The reaction mixture was poured into water (400 ml) and extracted with methylene chloride (2×150 ml). The aqueous layer was acidified to pH 2 with saturated aqueous oxalic acid and extracted with methylene chloride (2×200 ml). The non-acid impurities were removed by washing the organic layer with aqueous sodium hydrogen carbonate (18 g dissolved in 300 ml of water). The aqueous layer was washed one additional time with 100 ml of methylene chloride and then reacidified to pH 2 with aqueous oxalic acid. The aqueous layer was then extracted with methylene chloride (2×200 ml) and the organic extracts washed with water (150 ml), dried over anhydrous magnesium sulfate and evaporated to give 4.674 g of the title C compound as a light-yellow foam. $R_f$ 0.32 (1:1 hexane:ethyl acetate+1% HOAc).

D.

(1R*,2S*,4S*)-9,9-[Ethylenebis(oxy)]-1,2,3,4-tetrahydro-N-carbobenzyloxy-1,4-ethanonaphthalen-2-amine To a suspension of the title C compound (4.674 g, 17.95 mmol) in hexanes (110 ml) was added triethylamine (2.74 ml, 19.75 mmol). After stirring for 5 minutes at room temperature under argon, diphenylphosphoryl azide (4.24 ml, 19.75 mmol) was added and the resulting mixture stirred at room temperature for 15 minutes and at reflux for 45 minutes (slow evolution of nitrogen gas). At this point, benzyl alcohol (2.01 ml, 19.75 mmol) was added and the reaction mixture stirred at reflux for 15 hours. The reaction was cooled to room temperature and then poured into 5% citric acid (200 ml) along with ethyl ether (300 ml). The organic layer was washed with water (200 ml), saturated aqueous sodium hydrogen carbonate (200 ml) and brine (200 ml) and then dried over anhydrous magnesium sulfate. Evaporation gave an impure residue which was purified by flash chromatography (3:1 hexanes:ethyl acetate) resulting in 4.50 g of the title D compound as a white foam.

E.

(1R*,2S*,4S*)-9,9-[Ethylenebis(oxy)]-1,2,3,4-tetrahydro-N-carbobenzyloxy-N-methyl-1,4-ethanonaphthalen-2-amine To a suspension of potassium hydride/mineral oil(~8M) (2.46 ml, 19.70 mmol) in dry tetrahydrofuran (20 ml) under argon at room temperature was added a solution of the title D compound (2.40 g, 6.567 mmol) dissolved in tetrahydrofuran (4 ml). After 30 minutes, methyl iodide (4.41 ml, 65.67 mmol) was added and the mixture immediately warmed to 45°-50° C. A white solid (potassium iodide) began to precipitate from the reaction. After six hours, the reaction mixture was carefully poured into 150 ml of water stirring at ~0° along with ethyl ether (150 ml). After 5 minutes, the layers were separated and the aqueous layer extracted with additional ethyl ether (150 ml). The combined organic extracts were dried over anhydrous magnesium sulfate and evaporated to give a crude residue which was purified by flash chromatography (7:3 hexanes:ethyl acetate) resulting in 1.85 g of the title E compound as a colorless oil. $R_f$ 0.17 (3:1 hexane:ethyl acetate).

F.

(1R*,2S*,4S*)-1,2,3,4-Tetrahydro-N-carbobenzyloxy-9-oxo-N-methyl-1,4-ethanonaphthalen-2-amine To a stirring solution of the title E compound (2.44 g, 6.43 mmol) in tetrahydrofuran (55 ml) was added 2N hydrochloric acid (65 ml). The resulting cloudy mixture was stirred at room temperature for 21 hours. The reaction mixture was poured into brine (150 ml) and extracted with ethyl acetate (2×175 ml). The combined organic extracts were dried over sodium sulfate and evaporated to give a crude residue which was purified by flash chromatography (7:3 hexanes:ethyl acetate) to give 2.116 g of the title F compound as a viscous oil. $R_f$ 0.27 (96:4 methylene chloride: ethyl ether).

G.

(1R*,2S*,4S*,9S*)-1,2,3,4-Tetrahydro-9-(4-methoxyphenyl)-2-(carbobenzyloxy)-(methyl)amino-1,4-ethanonaphthalene-9-ol and (1R*,2S*,4S*,9R*)-1,2,3,4-Tetrahydro-9-(4-methoxyphenyl)-2-(carbobenzyloxy)-(methyl)amino-1,4-ethanonaphthalene-9-ol A suspension of anhydrous cerium (III) chloride (2.276 g, 1.5 eq., 9.20 mmol) was stirred in dry tetrahydrofuran (17 ml) at room temperature under argon for 2 hours. During this time, in a separate flask, 2.5M n-butyllithium/hexane (3.68 ml, 1.5 eq., 9.20 mmol) was added to a solution of 4-bromoanisole (1.39 ml, 1.8 eq., 11.058 mmol) in dry tetrahydrofuran (20 ml) at −78° C. under argon and the resulting cloudy solution stirred at that temperature for 1 hour. The cerium chloride/tetrahydrofuran slurry was cooled to −78° and the aryl lithium reagent prepared above added to it dropwise by means of a cannula. The aryl cerium reagent turned first yellow and then orange as it formed. The resulting mixture was stirred at −78° for 30 minutes at which point the title F compound (2.066 g, 6.159 mmol) dissolved in dry tetrahydrofuran (23 ml) was added. The orange color dissipated immediately. After stirring for 1 hour, the reaction was quenched with water (50 ml) and warmed to room temperature. The mixture was poured into additional water (150 ml) and extracted with ethyl ether (3×150 ml). The combined organic extracts were dried over anhydrous magnesium sulfate and evaporated to give a crude residue which was purified by flash chromatography (50 mm×7", 65:35 hexanes:ethyl acetate) to give 2.10 g of a white foam. The product consisted of ~2:1 mixture of isomers A and B by NMR. These isomers were separated on small scale by preparative TLC (93:7 methylene chloride: ethyl ether).

Isomer A: $R_f$ 0.21 (93:7 methylene chloride:ethyl ether).

Isomer B: $R_f$ 0.33 (93:7 methylene chloride:ethyl ether).

H.

(1R*,2S*,4S*,9S*)-1,2,3,4-Tetrahydro-9-(4-methoxyphenyl)-N-carbobenzyloxy-N-methyl-1,4-ethanonaphthalen-2-amine To a solution of a mixture of the title G isomers (1.40 g, 3.152 mmol) in dry methylene chloride (19 ml) at 0° under argon was added triethylsilane (1.01 ml, 2 eq., 6.304 mmol) followed by boron trifluoride etherate (0.77 ml, 2 eq., 6.304 mmol) dropwise. The resulting orange solution was stirred at 0° for 30 minutes. The reaction was quenched with saturated aqueous sodium carbonate (50 ml) and warmed to room temperature at which point the mixture was poured into additional saturated sodium carbonate (150 ml) and extracted wiht ethyl ether (3×200 ml). The combined organic extracts were dried over anhydrous magnesium sulfate and evaporated to give a crude residue which appeared to be a 85:10:5 mixture of the title H compound: styrene byproduct:diastereomer of the title H compound by NMR. This material was purified by flash chromatogrpahy (85:15 hexanes ethyl acetate followed by 3:1 hexanes:ethyl acetate) to give 0.81 g of pure title H product and 0.29 g of a mixture which was repurified by preparative TLC to give 1.00 g overall of the title H product as a viscous oil. $R_f$ 0.29 (3:1 hexane:ethyl acetate).

I.
(1R*,2S*,4S*,9S*)-1,2,3,4-Tetrahydro-9-(4-methoxyphenyl)-N-methyl-1,4-ethanonaphthalen-2-amine, monohydrochloride A suspension of the title H compound (1.308 g, 3.059 mmol), ammonium formate (0.95 g, 5 eq., 15.295 mmol) and 10% palladium on carbon (0.13 g) in methanol (32 ml) and absolute ethanol (5 ml) was stirred under a hydrogen atmosphere for 3 hours. The catalyst was filtered off on a pad of celite (methanol wash) and the filtrate evaporated. The resulting residue was dissolved in 200 ml of 1N sodium hydroxide and extracted with 3×100 ml of ethyl acetate. The combined organic extracts were dried over sodium sulfate and evaporated to give a crude residue which was purified by flash chromatography (93:7 methylene chloride:methanol) to give 0.85 g of a viscous oil. ($R_f$ 0.4 (9:1 methylene chloride:-methanol). The above oil (free base) (0.80 g, 2.726 mmmol) was dissolved in 30 ml of dry ethyl ether. Saturated $HCl/Et_2O$ was added until no additional solid formed. The solid was filtered and pumped dry to give 0.83 g of the title compound as a white powder, m.p. 254°–258° C.

Analysis calc'd for $C_{20}H_{24}ClNO$:
C, 72.82; H, 7.33; Cl, 10.75; N, 4.25; Found: C, 72.49; H, 7.33; Cl, 11.06; N, 4.29.

EXAMPLE 2
(1R*,2R*,4S*,9S*)-1,2,3,4-Tetrahydro-9-(4-methoxyphenyl)-N-methyl-1,4-ethanonaphthalen-2 -amine, monohydrochloride Starting with the exo isomer produced in part A of Example 1, and utilizing the procedure of steps B through I in Example 1, 0.95 g of the title compound as a white powder was prepared, m.p. >275° C.

Analysis calc'd for $C_{20}H_{24}ClNO \cdot 0.13 H_2O$:
C, 72.31; H, 7.36; Cl, 10.67; N, 4.22; Found: C, 72.42; H, 7.34; Cl, 10.50; N, 4.11.

EXAMPLE 3
(1R*,2R*,4R*,9R*)-1,2,3,4-Tetrahydro-9-(4-methoxyphenyl)-N-methyl-1,4-ethanonaphthalene-2-methanamine

A.
(1R*,2R*4S*)-9,9-[Ethylenebis(oxy)]-1,2,3,4-tetrahydro-N-methyl-N-(phenylmethyl)-1,4-ethanonaphthalene-2-methanamine A solution of 2M trimethyl aluminum in toluene (30 mL; 60 mmol) was added dropwise over 30 minutes to a solution of N-methylbenzylamine in 50 mL toluene at room temperature. After stirring an additional 30 minutes, a solution of the mixture of endo and exo isomers from part A of Example 1 (3:1, Endo:Exo) (5.76 g, 20 mmol) in 50 mL toluene was added in one portion and the reaction was heated to 70° C. for 18 hours. At this time, 1N hydrochloric acid was added with extreme care until all foaming ceased. The mixture was then extracted with ethyl acetate (~500 mL) and the resulting organic layer was washed with saturated sodium hydrogen carbonate solution, followed by brine. After drying over anhydrous magnesium sulfate and concentration, the crude residue was chromatographed using Hexane:ethyl acetate, 3:2 as the eluent. The product containing fractions were concentrated to afford 4.6 g of an intractable mixture of the tertiary amides. A solution of the amides (4.60 g; 12.7 mmol) in 100 mL ethyl ether was added dropwise over 30 minutes to a suspension of lithium aluminum hydroxide (12.10 g, 28 mmol) in 150 mL of ethyl ether at room temperature. After stirring an additional 30 minutes, 1.1 mL of water was added very carefully, followed by 1.1 mL of 15% sodium hydroxide solution, followed by an additional 3.3 mL of water. At this time, the white granular precipitate was filtered and washed thoroughly with ethyl ether. The filtrate was concentrated to afford 4.43 g of a mixture of endo and exo tertiary amines. After three silica gel chromatographies using Hexane:ethyl acetate, 4:1, 1.55 g, endo, 1.95 g exo and 0.93 g of mixed material was isolated. The title A endo-isomer was carried on to complete this synthesis.

B.
(1R*,2R*4S*)-1,2,3,4-Tetrahydro-N-methyl-9-oxo-N-(phenylmethyl)-1,4-ethanonaphthalene-2-methan amine A mixture of the title A compound (1.53 g, 4.4 mmol) in 2N hydrochloric acid (48 mL) and tetrahydrofuran (40 mL) was stirred at room temperature for 18 hours. The tetrahydrofuran was removed in vacuo and the remaining aqueous mixture was basified to pH 13. After extracting the basic mixture with ethyl acetate (2×200 mL), the organic phase was washed with brine (2×50 mL), and dried with magnesium sulfate. Concentration afforded 1.32 g of the title B compound as a colorless oil.

C.
(1R*,2R*,4S*,9R*)-1,2,3,4-Tetrahydro-9-(4-methoxyphenyl)-2-[[methyl-(phenylmethyl)am ino]methyl]-1,4-ethanonaphthalene-9-ol and

D.
(1R*,2R*,4S*,9S*)-1,2,3,4-Tetrahydro-9-(4-methoxyphenyl)-2-[[methyl-(phenylmethyl)am ino]methyl]-1,4-ethanonaphthalene-9-ol A suspension of cerium chloride (1.13 g, 4.6 mmol) was stirred in 7 mL of freshly distilled tetrahydrofuran for 2 hours at room temperature. During this time in a separate flask, a solution of p-methoxyphenyl lithium was prepared by adding n-butyl lithium (1.84 mL of 2.5M Hexane solution; 4.6 mmol) dropwise (5 minutes) to a solution of p-bromoanisole in 7 mL of tetrahydrofuran at −78° C. and stirred for 1 hour. The cerium chloride suspension was cooled to −78° C. and the p-methoxyphenyl lithium solution was added via a cannula. An orange suspension resulted and after 30 minutes, the title B compound (635 mg, 2.1 mmol) was added as a solution in 7 mL of tetrahydrofuran. The orange color dulled slightly. After 1 hour at −78° C., water (~20 mL) was added and the mixture was extracted with ethyl ether (2×75 mL). The organic layer was washed with brine, dried over anhydrous magnesium sulfate and concentrated. The residue was flashed on a (5 ×20 cm) silicon oxide column using ethyl acetate: hexane (1:3) as the mobile phase. Concentration of the early fractions afforded 580 mg, of the title C compound as a white solid. The later fractions were concentrated to afford 85 mg, of the title D compound as a colorless oil.

E.
(1R*,2R*,4R*,9R*)-1,2,3,4-Tetrahydro-9-(4-methoxyphenyl)-N-methyl-N-(phenylmethyl)-1,4-ethanonaphthalene-2-methanamine F.
(1R*,2R*,4R*,9S*)-1,2,3,4-Tetrahydro-9-(4-methoxyphenyl)-N-methyl-N-(phenylmethyl)-1,4-ethanonaphthalene-2-methanamine and G.
(1R*,2R*,4R*)-1,4-Dihydro-9-(4-methoxyphenyl)-N-methyl-N-(phenylmethyl)-1,4-ethanonaphthalene-2-methanamine Boron trifluoride etherate (1.28 mL; 10.4 mmol) was added dropwise over 5 minutes to a solution of compounds C and D (1.95 g, 4.71 mmol) and triethylsilane (1.66 mL, 10.4 mmol) at 0° C. in 35 mL of methylene chloride. After stirring for 30 minutes at 0° C., the reaction mixture was partitioned between saturated sodium carbonate solution (300 mL) and ethyl ether (600 mL). The separated ethyl ether layer was dried over anhydrous magnesium sulfate and concentrated to 1.8 g of crude oil. The crude material was flash chromatographed on a 5×25 cm silicon oxide column using ethyl acetate:hexane, 15:85 as the mobile phase. Concentration of the product containing fractions afforded 1.58 g, 85% yield of a mixture of compounds E, F and G. The crude mixture of products was separated by preparative TLC. (A single 1 mm thick, 20×20 cm plate, double eluted with ethyl acetate:hexane, 1:1). Extraction of the less polar band afforded 52 mg of the title E compound contaminated with a trace of the title F compound. Extraction of the more polar band afforded 33 mg of the title G compound, contaminated with a small amount of the title F compound.

H.
(1R*,2R*,4R*,9R*)-1,2,3,4-Tetrahydro-9-(4-methoxyphenyl)-N-methyl-1,4-ethanonaphthalene-2-methanamine A solution of the title E, F and G compounds (1.565 g, 3.95 mmol) in 30 mL of acetaldehyde was hydrogenated over 20% Pd(OH)$_2$ on carbon for 24 hours at room temperature using a balloon apparatus. The catalyst was filtered through celite and the filtrate was concentrated to dryness. The residue was partitioned between 1N sodium hydroxide and ethyl acetate. The ethyl acetate layer was washed with brine (2×100 mL) and dried over sodium sulfate. After concentration the residue was flashed on a 5×15 cm silicon oxide column as follows: 1 L 5% MeOH/CH$_2$Cl$_2$, 1 L 10% MeOH/CH$_2$Cl$_2$, 1 L 20% MeOH/CH$_2$Cl$_2$. Since it was impossible to monitor the purity of fractions by TLC, arbitrary cuts were taken and monitored by NMR. Concentration of the early fractions afforded 562 mg of the free base of the title compound which was pure by NMR. The middle fractions were concentrated to afford 283 mg of very slightly impure free base. The later fractions were concentrated to afford 265 mg of a mixture of free base. (Total yield of reaction—1.102 g).

The free base (510 mg, 1.66 mmol) was dissolved in ethyl ether/methanol and excess ethereal hydrochloric acid was added. The resulting solution was concentrated and the residue was triturated with ethyl ether/ethyl acetate and dried to afford 530 mg of the title product as a white powder.

Another portion of the free base (275 mg, 0.9 mmol) was dissolved in ethyl acetate. Ethereal hydrochloric acid (3 ml) was added and ethyl ether was added until a precipitant formed. Filtration and drying afforded 280 mg of the title product as a white powder which was pure by NMR and HPLC. Therefore this batch was combined with the one above to afford 810 mg, m.p. 197°–199° C.

Analysis calc'd for C$_{21}$H$_{26}$ClNO:
C, 73.34; H, 7.62; N, 4.07; Cl, 10.31; Found: C, 72.96; H, 7.60; N, 4.00; Cl, 10.48.

EXAMPLE 4

(1R*,2S*,4R*,9R*)-1,2,3,4-Tetrahydro-9-(4-methoxyphenyl)-N-methyl-1,4-ethanonaphthalene-2-methanamine, monohydrochloride A.
(1R*,2S*,4S*)-1,2,3,4-Tetrahydro-N-methyl-9-oxo-N-(phenylmethyl)-1,4-ethanonaphthalene-2-metha namine A mixture of the title A Endo Isomer of Example 3 (2.33 g, 6.71 mmol) in 2N hydrochloric acid (73 ml) and tetrahydrofuran (60 ml) was stirred at room temperature for 18 hours. The tetrahydrofuran was removed in vacuo and the remaining aqueous mixture was basified to pH 13 with 1N sodium hydroxide. After extracting the basic mixture with ethyl acetate (2×250 ml), the organic phase was washed with brine (2×50 ml) and dried with magnesium sulfate. Concentration afforded 2.01 g of the title A compound as a colorless oil.

B.
(1R*,2S*,4S*,9R*)-1,2,3,4-Tetrahydro-9-(4-methoxyphenyl)-2-[[methyl-(phenylmethyl)am ino]methyl]-1,4-ethanonaphthalene-9-ol and C.
(1R*,2S*,4S*,9S*)-1,2,3,4-Tetrahydro-9-(4-methoxyphenyl)-2-[[methyl-(phenylmethyl)am ino]methyl]-1,4-ethanonaphthalene-9-ol A suspension of cerium chloride (1.13 g, 4.6 mmol) was stirred in 7 ml of freshly distilled tetrahydrofuran for 2 hours at room temperature. After stirring the cerium chloride suspension one hour, a solution of p-methoxyphenyl lithium was prepared by adding n-butyl lithium (1.84 ml of 2.5M hexane solution; 4.6 mmol) dropwise (over 5 minutes) to a solution of p-bromoanisole in 7 ml of tetrahydrofuran at −78° C. At the end of 2 hours, the cerium chloride suspension was cooled to −78° C. and the p-methoxyphenyl lithium solution was added via a cannula. An orange suspension resulted and after 30 minutes, the title A compound (635 mg, 2.1 mmol) was added as a solution in 7 ml of tetrahydrofuran. The orange color dulled slightly After 1 hour at −78° C., water (∼20 ml) was added and the mixture was extracted with ethyl ether (2×75 ml). The organic layer was dried over anhydrous magnesium sulfate and concentrated to afford a semisolid, which was triturated with hexane to afford 425 mg of the title B compound as a white solid. The mother liquor was concentrated and the residue was purified via preparative TLC (silica gel, two 1 mm plates, ethyl acetate:hexane, 1:2). Extraction of the less polar band afforded 170 mg of the title B compound while extraction of the more polar band afforded 30 mg of the title C compound.

D.
(1R*,2S*,4R*,9R*)-1,2,3,4-Tetrahydro-9-(4-methoxyphenyl)-N-methyl-N-(phenylmethyl)-1,4-ethanonaphthalene-9-ol E.
(1R*,2S*,4R*,9S*)-1,2,3,4-Tetrahydro-9-(4-methoxyphenyl)-N-methyl-N-(phenylmethyl)-1,4-ethanonaphthalene-2-methanamine and F.
(1R*,2S*,4R*)-1,4-dihydro-9-(4-methoxyphenyl)-N-methyl-N-(phenylmethyl)-1,4-ethanonaphthalene-2-methanamine Boron trifluoride etherate (0.8 ml, 6.53 mmol) was added over 3 minutes to a stirred solution of the title C compound(1.23 g, 2.97 mmol) and triethyl silane (1.04 ml, 6.53 mmol) in 25 ml of methylene chloride at 0° C. After stirring 30 minutes the reaction was quenched with 250 ml of saturated sodium carbonate solution. After extracting with ethyl ether (250 ml), 25 ml of 1N sodium hydroxide was added to the aqueous layer. This layer was extracted with ether (150 ml) and the combined organic layers were washed with brine (75 ml), dried over anhydrous magnesium sulfate and concentrated to a crude residue. After combining this residue with the residue from a small scale run the crude mixture was flash chromatographed on a 5×15 cm silicon oxide column using hexane:ethyl acetate, 9:1 as the eluent. Concentration of product containing fractions afforded 1.32 g of a mixture of the title D, E and F compounds.

G.
(1R*,2S*,4R*,9R*)-1,2,3,4-Tetrahydro-9-(4-methoxyphenyl)-N-methyl-1,4-ethanonaphthalene-2-methanamine, monohydrochloride The title D, E and F compounds (1.20 g, 3.02 mmol) were hydrogenated at atmospheric pressure and at room temperature over 20% Pd(OH)$_2$/C (200 mg) in 30 ml of acetic acid for 18 hours. The reaction mixture was filtered through celite and the filter cake was washed with acetic acid. The filtrate was concentrated to dryness and the residue was partitioned between ethyl acetate (400 ml) and 1N sodium hydroxide (250 ml). The organic layer was washed with brine, dried over sodium sulfate and concentrated. The residue was flash chromatographed as follows on a 5×15 cm silica gel column; 2 L 5% MeOH/CH$_2$Cl$_2$, 2 L 10% MeOH/CH$_2$Cl$_2$, 2 L 15% MeOH/CH$_2$Cl$_2$. The pure fractions were concentrated to afford 410 mg of free base. The impure fractions were concentrated to afford 325 mg of material which was subsequently purified by preparative TLC. (Two 1 mm silica plates eluted with CH$_2$Cl$_2$:MeOH:NH$_4$OH, 90:1:1.) Extraction of the pure band with (CH$_2$Cl$_2$:MeOH, 9:1) and concentration afforded 190 mg of additional free base for a total yield of the title compound of 600 mg.

The combined free base material was taken up in ethyl ether:ethyl acetate:methanol, ~7:2:1 to afford a turbid mixture, this was filtered through celite and ethereal HCl (~10 ml) was added. The solid was filtered and dried to afford 500 mg of the title compound as a white powder, m.p. 209°-211° C. (Dec.).

Analysis calc'd for C$_{21}$H$_{25}$NO.HCl:
C, 73.34; H, 7.62; N, 4.07; Found: C, 73.01; H, 7.61; N, 3.84.

EXAMPLE 5
(1R*,2R*,4S*,9R*)-1,2,3,4-Tetrahydro-9-(4-methoxyphenyl)-N-methyl-1,4-ethanonaphthalen-2-amine, monohydrochloride To 126 mg (0.429 mmol) of the title compound from Example 2 in 25 mL of ethyl ether was added an excess of saturated HCl/Et$_2$O. The resulting white solid was filtered and pumped to give 137 mg of the title compound, m.p. 248°-253° C. dec.).

Analysis calc'd for C$_{20}$H$_{24}$NOCl.0.21 H$_2$O:
C, 71.99; H, 7.37; N, 4.20; Cl, 10.62; Found: C, 71.88; H, 7.24; N, 4.00; Cl, 10.93.

EXAMPLE 6
(1R*,2R*,4S*,9S*)-1,2,3,4-Tetrahydro-9-(4-methoxyphenyl)spiro[1,4-ethanonaphthalene-2, 3'-pyrrolidine], monohydrochloride A.
(1R*,2S*,4R*)-9,9-[Ethylenebis(oxy)]-1,2,3,4-tetrahydro-1,4-ethanonaphthalene-2-(2-propenyl)-2-carboxylic acid ethyl ester and B.
(1R*,2R*,4R*)-9,9-[Ethylenebis(oxy)]-1,2,3,4-tetrahydro-1,4-ethanonaphthalene-2-(2-propenyl)-2-carboxylic acid ethyl ester A 2.5M solution of n-butyl lithium in hexane (5.9 ml, 14.6 mmol) was added to a solution of diisopropyl amine in 25 ml tetrahydrofuran at 0° C. After stirring 10 minutes at 0° C., the resulting solution of lithium diisopropyl amide was cooled to −78° C. A mixture of the endo and exo isomers (3:1) from part A of Example 1 (2.78 g, 9.7 mmol) was then added dropwise as a solution in 25 ml of tetrahydrofuran over 15 minutes. After stirring 1 hour at −78° C., allyl bromide was added over 5 minutes. The reaction was stirred for 3 hours during which time the temperature was allowed to rise from −78° C. to −40° C. After partitioning the reaction mixture between ethyl ether (200 ml) and brine (200 ml), the organic layer was dried over magnesium sulfate and concentrated to an oily residue. This residue was flash chromatographed on a 5×18 cm silica gel column, using 15% ethyl acetate/hexane as the solvent system. The less polar fractions were concentrated to afford 0.78 g of the title B compound as a colorless solid. R$_f$=0.44, ethyl acetate:hexane, 1:3, m.p. 65°-67.5° C. The more polar fractions were concentrated to afford 2.08 g of the title A compound as a colorless oil. R$_f$=0.38, ethyl acetate:hexane, 1:3.

C.
(1R*,2R*,4R*)-9,9-[Ethylenebis(oxy)]-1,2,3,4-tetrahydro-1,4-ethanonaphthalene-2-(2-oxoethyl)-2-carboxylic acid ethyl ester An ozone/oxygen mixture was bubbled through a suspension of the title B compound (4.37 g, 13.3 mmol) and sodium bicarbonate (0.11 g, 1.33 mmol) in methanol for 30 minutes at −78° C. Dimethyl sulfide (10 ml) was added and the reaction mixture was allowed to warm to room temperature. After stirring 18 hours, the reaction mixture was concentrated and the residue was partitioned between water (150 ml) and ethyl ether (250 ml). The organic layer was washed with brine and dried over magnesium sulfate. Concentration afforded 4.40 g of the title C compound as a colorless oil. R$_f$=0.15, ethyl acetate:hexane, 1:3.

D.
(1R*,2R*,4R*)-9,9-[Ethylenebis(oxy)]-1,2,3,4-tetrahydro-1,4-ethanonaphthalene-2-[[2-(phenylmethyl)amino]ethyl]-2-carboxylic acid ethyl ester Dilute methanolic HCl (~350 ml) was added to benzyl amine (2.85 ml, 26 mmol) with stirring until a pH of 6 was attained as monitored by wet pH paper. The title C compound (4.3 g, 13 mmol) was added as a solution in methanol (~50 ml), followed by a 3Å molecular sieves (6.85 g) and sodium cyanoborohydride (0.86 g, 13 mmol). After stirring 20 hours, the cloudy reaction mixture was filtered through celite and the filtrate was concentrated. The residue was partitioned between ethyl acetate (500 ml) and 0.5M sodium hydroxide (300 ml). The organic layer was washed with brine, dried over magnesium sulfate and concentrated. The residue was flashed on a 5×15 cm silica gel column using ethyl acetate as the solvent system. The pure fractions were concentrated to afford 4.25 g of the title D compound as a colorless solid, m.p. 159°-162° C.

E.
(1R*,2R*,4R*)-9,9-[Ethylenebis(oxy)]-1,2,3,4-tetrahydro-N-(phenylmethyl)-spiro-[1,4-ethanonaphthalene-2,3'-pyrrolidinone]

A mixture of the title D compound (4.2 g, 10.4 mmol) and 25% sodium methoxide in methanol (3.6 ml, 15.6 mmol) was refluxed in 110 ml of methanol for 3 hours. After cooling, the reaction mixture was diluted with ethyl acetate (500 ml) and the resultant organic mixture was washed with 1N hydrochloric acid (300 ml), saturated sodium bicarbonate solution (100 ml) and brine (100 ml). After drying over magnesium sulfate, the organic layer was concentrated to afford 3.24 g of the title E compound as a white solid, m.p. 164°-166° C. $R_f = 0.75$, ethyl acetate

F.
(1R*,2R*,4R*)-9,9-[Ethylenebis(oxy)]-1,2,3,4-tetrahydro-N-(phenylmethyl)-spiro-[1,4-ethanonaphthalene-2,3'-pyrrolidine-]

A solution of the title E compound (3.11 g, 8.3 mmol) in 40 ml of tetrahydrofuran and 40 ml of ethyl ether was added dropwise to a suspension of lithium aluminum hydride (1.4 g, 35 mmol) in 170 ml of ethyl ether at room temperature. This addition took approximately 30 minutes. After stirring 1 hour, the reaction mixture was cooled to 0° C. and 1.5 ml of water was added dropwise with extreme caution. The addition of water was followed by an addition of 1.5 ml of 15% sodium hydroxide solution and another 4.5 ml of water. Ethyl ether and magnesium sulfate were then added. Filtration of the granular suspension and concentration of the filtrate afforded 3.08 g ($\leq 100\%$) of the title F compound as a white solid, m.p. 81°-84° C. $R_f = 0.38$, ethyl acetate.

G.
(1R*,2R*,4R*)-1,2,3,4-Tetrahydro-9-oxo-N-(phenylmethyl)-spiro[1,4-ethanonaphthalene-2,3'-pyrrolidine]

A mixture of the title F compound (2.9 g, 8.03 mmol) and 2N hydrochloric acid (90 ml) in 80 ml of tetrahydrofuran was stirred at room temperature for 18 hours. The tetrahydrofuran was removed in vacuo and the remaining aqueous mixture was basified to pH >12. After extraction with ethyl acetate (300 ml), the organic layer was washed with brine (200 ml), dried with magnesium sulfate and concentrated to afford 2.53 g of the title G compound as a colorless oil. $R_f = 0.38$ ethyl acetate.

H.
(1R*,2R*,4R*,9S*)-1,2,3,4-Tetrahydro-9-(4-methoxyphenyl)-(phenylmethyl)-spiro[2,3'-pyrrolidino]-1,4-ethanonaphthalene-9-ol and

I.
(1R*,2R*,4R*,9R*)-1,2,3,4-Tetrahydro-9-(4-methoxyphenyl)-(phenylmethyl)-spiro[2,3'-pyrrolidino]-1,4-ethanonaphthalene-9-ol A suspension of cerium chloride (4.3 g, 17.4 mmol), was stirred in 33 ml of freshly distilled tetrahydrofuran for 2 hours at room temperature. After stirring the cerium chloride suspension 1 hour, a solution of p-methoxyphenyl lithium was prepared by adding n-butyl lithium (7.25 ml of a 2.5M hexane solution; 17.4 mmol) dropwise (over 5 minutes) to a solution of p-bromoanisole (2.4 ml, 19 mmol) in 33 ml of tetrahydrofuran −78° C. At the end of 2 hours, the cerium chloride suspension was cooled to −78° C. and the p-methoxyphenyl lithium solution was added rapidly through a cannula. An orange suspension resulted and after 30 minutes, the title G compound was added as a solution in 33 ml of tetrahydrofuran. The orange color dulled slightly. After 1 hour at −78° C., water was added (100 ml) and the mixture was extracted with ethyl ether (2×100 ml). The combined organic layer was washed with brine (100 ml) and dried over magnesium sulfate. After concentration, the residue was flash chromatographed on a 5×15 cm silica gel column, using the following elution scheme: 2 L hexane:ethyl acetate, 65:35, 1 L hexane:ethyl acetate, 50:50, and 1 L hexane:ethyl acetate, 30:70. Concentration of the pure less polar fractions afforded 2.34 g of the title H compound as a white solid. $R_f = 0.29$, ethyl acetate:hexane, 1:1, m.p. 104°-106° C. Concentration of the pure more polar fractions afforded 0.54 g of the title I compound as a colorless oil. $R_f = 0.06$, ethyl acetate:hexane, 1:1.

J.
(1R*,2R*,4S*,9S*)-1,2,3,4-Tetrahydro-9-(4-methoxyphenyl)-N-(phenylmethyl)-spiro[1,4-ethanonaphthalene-2,3'-pyrrolidine

K.
(1R*,2R*,4S*,9R*)-1,2,3,4-Tetrahydro-9-(4-methoxyphenyl)-N-(phenylmethyl)-spiro[1,4-ethanonaphthalene-2,3'-pyrrolidine and

L.
(1R*,2S*,4R*)-1,2,3,4-Tetrahydro-9-(4-methoxyphenyl)-N-(phenylmethyl)-spiro[1,4-ethenonaphthalene-2,3'-pyrrolidine]

Boron trifluoride etherate (1.4 ml, 11.2 mmol) was added dropwise over 5 minutes to a solution of the title H compound (2.15 g, 5.1 mmol) and triethylsilane (1.8 ml, 11.2 mmol) in 50 ml of methylene chloride at 0° C. After stirring 1 hour, the reaction was quenched with saturated sodium carbonate solution and extracted with ethyl ether (500 ml). The organic layer was dried over magnesium sulfate and concentrated to afford a crude residue which was flash chromatographed on a 5×15 cm silica gel column. Elution with hexane:ethyl acetate, 9:1 afforded partial separation. The pure less polar fractions were concentrated to afford 0.665 g of the title J compound. The apparently pure more polar fractions were concentrated to afford 0.06 g of a mixture of the title K and L compounds. The mixed fractions were rechomatographed using the same conditions as above. Concentration of the pure less polar fractions afforded an additional 0.372 g of the title J compound. (Total pure—1.037 g). $R_f$=0.17, hexane:ethyl acetate, 2:1. Concentration of the pure more polar fractions afforded 0.470 g of a mixture of the title K and L compounds, 86:14. (Total—0.530 g). $R_f$=0.11, hexane:ethyl acetate, 2:1. Concentration of the mixed fractions afforded 0.228 g.

M.
(1R*,2R*,4S*,9S*)-1,2,3,4-Tetrahydro-9-(4-methoxyphenyl)spiro[1,4-ethanonaphthalene-2,3'-pyrrolidine], monohydrochloride The title J compound (0.920 g, 2.25 mmol) was hydrogenated, using a balloon apparatus, over 20% palladium hydroxide on carbon in 20 ml of 95% ethanol and 10 ml of ethyl acetate at room temperature for 18 hours. The catalyst was removed by filtration through a millipore filter and the filtrate was concentrated to afford 0.727 g of the free base as a colorless oil.

The free base (0.69 g, 2.16 mmol) was dissolved in ~10 ml of methanol. An excess of ethereal HCl was added and the mixture was concentrated to a white solid which was crystallized from methanol/ethyl ether. Filtration and drying under high vacuum at room temperature afforded 0.601 g of the title compound as a colorless crystalline solid, m.p. >255° C., $R_f$=0.60, n-butanol:acetic acid:water:ethyl acetate, 1:1:1:3.

Analysis calc'd for $C_{22}H_{25}NO \cdot HCl \cdot 0.2\ H_2O$:
C, 73.4g; H, 7.40; N, 3.90; Cl, 9.87 Found: C, 73.87; H, 7.49; N, 3.56; Cl, 9.75.

EXAMPLE 7
(1R*,2S*,4R*)-1,2,3,4-Tetrahydro-9-(4-methoxyphenyl)spiro-[1,4-ethenonaphthalene-2,3'-pyrrolidine], monohydrochloride α-Chloroethylchloroformate was added to a solution of the title L compound of Example 6 (0.362 g, 0.89 mmol) in 1,2-dichloroethane at 0° C. After stirring 15 minutes at 0° C., the reaction mixture was heated to reflux for 1.5 hours. The solvents were removed in vacuo and the residue was refluxed in methanol for 1 hour. After cooling to room temperature, ~5 ml of ethereal hydrochloric acid was added and the mixture was concentrated to dryness. The residue was chromatographed on a 2.5 ×15 cm HP-20 column as follows: (1) 100 ml 0.2% AcOH, (2) 100 ml 0.2% AcOH:MeOH, 9:1, (3) 100 ml 0.2% AcOH:MeOH, 8:2, (4) 100 ml 0.2% AcOH:MeOH, 7:3, (5) 100 ml 0.2% AcOH:MeOH, 6:4, (6) 100 ml 0.2% AcOH:MeOH, 5:5, (7) 100 ml 0.2% AcOH:MeOH, 4:6, (8) 200 ml 0.2% AcOH:MeOH, 3:7, (9) 100 ml 0.2% AcOH:MeOH, 2:8, (10) 100 ml 0.2% AcOH:MeOH, 1:9, (11) 300 ml MeOH. The pure fraction were concentrated. The residue was dissolved in methanol and ~5 ml of ethereal HCl was added. Ethyl ether was added until the solution became cloudy. After standing at −20° C. for several hours, the precipitant that formed was filtered and dried to afford 0.19 g of a white solid. $^1$H NMR and HPLC of this material indicated the presence of significant impurities. The solid was recrystallized from MeOH/Et$_2$O to afford 0.17 g of the title compound as a colorless crystalline solid, m.p. 175°-178° C. $R_f$=0.56, n-BuOH:AcOH:H$_2$O:EtOAc, 1:1:1:3.

Analysis calc'd for $C_{22}H_{23}NO_2 \cdot HCl \cdot 0.34\ H_2O$:
C, 73.40; H, 6.91; N, 3.89; Cl, 9.85; Found: C, 73.68; H, 6.88; N, 3.61; Cl, 9.49.

EXAMPLE 8
(1R*,2S*,4S*,9S*)-1,2,3,4-Tetrahydro-9-(4-methoxyphenyl)spiro[1,4-ethanonaphthalene-2, 3'-pyrrolidine], monohydrochloride

A.
(1R*,2S*,4R*)-9,9-[Ethylenebis(oxy)]-1,2,3,4-tetrahydro-1,4-ethanonaphthalene-2-(2-propenyl)-2-[N-(phenylmethyl)]carboxylic acid amide A 2M solution of trimethylaluminum in toluene (42 ml, 84 mmol) was added dropwise over 20 minutes to a solution of benzylamine (9.2 ml, 84 mmol) in 100 ml of toluene at 0° C. This mixture was warmed to room temperature and stirred for 1 hour. At this time the title A ester of Example 6 (5.52 g, 16.8 mmol) was added in one portion as a solution in 70 ml of toluene. After refluxing for 20 hours, the reaction mixture was cooled to 0° C. and 1N hydrochloric acid (200 ml) was added dropwise very cautiously to minimize foaming. The mixture was extracted with ethyl acetate (400 ml) and the organic layer was washed with 1N hydrochloric acid (150 ml), saturated sodium bicarbonate solution (150 ml), and brine (150 ml). After drying over magnesium sulfate, the organic layer was concentrated to an off-white solid which was recrystallized from ethyl acetate/hexane to afford 4.44 g of the title A amide as a white solid, m.p. 161°-164° C.

B.
(1R*,2S*,4R*)-9,9-[Ethylenebis(oxy)]-1,2,3,4,-tetrahydro-N-(phenylmethyl)-spiro-[1,4-ethanonaphthalene-2,3'-pyrrolidine]and

C.
(1R*,2S*,4R*)-9,9-[Ethylenebis(oxy)]-1,2,3,4-tetrahydro-1,4-ethanonaphthalene-2-(2-hydroxyethyl)-[N-(phenylmethyl)]carboxylic acid amide Sodium bicarbonate (0.076 g, 0.9 mmol) was added to a solution of the title A amide (3.426 g, 8.8 mmol) in 70 ml of methylene chloride. The mixture was cooled to −78° C. and an ozone/oxygen mixture was bubbled through the solution until a blue color was observed (~15 minutes). At this time, the reaction mixture was purged with oxygen until the blue color dissipated. Methanol (15 ml) and sodium borohydride (2 g, 51 mmol) were added and the reaction was allowed to warm to room temperature. After stirring 1 hour, the reaction mixture was partitioned between methylene chloride (~150 ml) and brine (~150 ml). The aqueous layer was extracted with methylene chloride (~150 ml) and the combined organic layers were dried over magnesium sulfate. After concentration, the residue was flash chromatographed on a 5×15 cm silica gel column which was eluted with ethyl acetate:hexane, 3:2. Concentration of the less polar fractions afforded 1.075 g of the title B compound pyrrolide as a colorless oil. Concentration of the more polar fractions afforded 1.50 g of the title C alcohol.

D.
(1R*,2S*,4R*)-1,2,3,4-Tetrahydro-9-oxo-N-(phenylmethyl)-spiro[1,4-ethanonaphthalene-2,3'-pyrrolidine A mixture of the title B pyrrolidine (1 g, 2.8 mmol), 2N hydrochloric acid (32 ml) and tetrahydrofuran was stirred at room temperature for 18 hours. The tetrahydrofuran was removed in vacuo and the remaining aqueous mixture was basified to pH >13 with 3N potassium hydroxide. This basic layer was extracted with ethyl acetate. The organic layer was then washed with brine, dried over magnesium sulfate and concentrated to afford 0.951 g of the title D ketone as an oil.

E.
(1R*,2S*,4R*,9S*)-1,2,3,4-Tetrahydro-9-(4-methoxyphenyl)-(phenylmethyl)-spiro[2,3'-pyrrolidino]-1,4-ethanonaphthalene-9-ol and

F.
(1R*,2S*,4R*,9R*)-1,2,3,4-Tetrahydro-9-(4-methoxyphenyl)-(phenylmethyl)-spiro[2,3'-pyrrolidino]-1,4-ethanonaphthalene-9-ol A suspension of cerium chloride (1.70 g, 6.9 mmol) was stirred in 9 ml of freshly distilled tetrahydrofuran for 2 hours at room temperature. After stirring the cerium chloride suspension 1 hour, a solution of p-methoxyphenyl lithium was prepared by adding n-butyl lithium (2.80 ml of a 2.5M hexane solution; 6.93 mmol) dropwise (over 5 minutes) to a solution of p-bromoanisole (0.95 ml, 7.6 mmol) in 9 ml of tetrahydrofuran at −78° C. At the end of 2 hours, the cerium chloride suspension was cooled to −78° C. and the p-methoxyphenyl lithium solution was added rapidly through a cannula. An orange suspension resulted and after 30 minutes the title D ketone (0.88 g, 2.77 mmol) was added as a solution in 9 ml of tetrahydrofuran. After stirring 30 minutes at −78° C., water was added and the mixture was extracted with ethyl ether (2×150 ml). The organic layer was dried over magnesium sulfate and concentrated to afford a residue which was flash chromatographed on a 5×15 cm silica gel column. Elution with ethyl acetate:hexane, 3:1 and concentration of product containing fractions afforded 0.90 g of a mixture of the title E and F alcohols in a ratio of 2:1.

G.
(1R*,2S*,4S*,9S*)-1,2,3,4-Tetrahydro-9-(4-methoxyphenyl)-N-(phenylmethyl)-spiro[1,4-ethanonaphthalene-2,3'-pyrrolidine]

H.
(1R*,2S*,4S*,9R*)-1,2,3,4-Tetrahydro-9-(4-methoxyphenyl)-N-(phenylmethyl)-spiro[1,4-ethanonaphthalene-2,3'-pyrrolidine and

I.
(1R*,2R*,4R*)-1,2,3,4-Tetrahydro-9-(4-methoxyphenyl)-N-(phenylmethyl)-spiro[1,4-ethenonaphthalene-2,3'-pyrrolidine]

Boron trifluoride etherate (0.57 ml, 4.6 mmol) was added dropwise over 10 minutes to a solution of the title E and F alcohols (0.89 g, 2.1 mmol) and triethylsilane (0.74 ml, 4.6 mmol) in 20 ml of methylene chloride at 0° C. After stirring 1 hour, the reaction mixture was quenched with ∼10 ml of saturated sodium carbonate solution. The quenched mixture was partitioned between ethyl ether and saturated sodium carbonate solution. The organic layer was dried over magnesium sulfate and concentrated to afford 0.84 g of a mixture of the title G, H and I compounds as a colorless oil which was used in the next step without further purification.

J.
(1R*,2S*,4S*,9S*)-1,2,3,4-Tetrahydro-9-(4-methoxyphenyl)spiro[1,4-ethanonaphthalene-2,3'-pyrrolidine], monohydrochloride A mixture of the title G, H and I compounds (0.83 g, 2.03 mmol) was hydrogenated over 20% palladium hydroxide on carbon (200 mg) for 24 hours in 20 ml of acetic acid at atmospheric pressure. At the end of this time, starting material remained by TLC. An additional 50 mg of catalyst was added and the mixture was hydrogenated for 18 hours. The catalyst was removed by filtration and the filtrate was concentrated to dryness. The residue was partitioned between 1N sodium hydroxide and ethyl acetate. After drying over sodium sulfate, the organic layer was concentrated to dryness. The residue was flash chromatographed on a 5×12 cm silica gel column which was eluted as follows; 1 L CH$_2$Cl$_2$, 1 L 5% MeOH/CH$_2$Cl$_2$, 1 L 10% MeOH/CH$_2$Cl$_2$, 1 L 15% MeOH/CH$_2$Cl$_2$, 1 L 20% MeOH/CH$_2$Cl$_2$, 1 L CH$_2$Cl$_2$:MeOH:NH$_4$OH, 90:19:1. The product containing fractions were concentrated to afford 0.35 g of a brown foam which was treated with excess ethereal HCl in MeOH. After concentration the solid residue was crystallized from ethanol/ethyl ether to afford 0.18 g of the title compound. The column described above was washed with an additional 1 L of CH$_2$Cl$_2$:MeOH:NH$_4$OH, 90:19:1 and the resulting eluent was concentrated to afford 0.28 g of an off white foam. This residue was combined with the mother liquor from the crystallization described above. This mixture was treated with excess ethereal hydrochloric acid and the resulting solution was concentrated to afford a white solid. This solid was triturated with water, filtered, washed with ethyl ether, and dried to afford an additional 0.118 g of the title compound. The two batches were combined and homogenated to afford 0.298 g of the title compound, m.p. 187°–189° C. (dec).

Analysis calc'd for C$_{22}$H$_{25}$NO.HCl 0.9H$_2$O:
C, 71.00; H, 7.53; N, 3.76; Cl, 9.52; Found: C, 71.12; H, 7.39; N, 3.55; Cl, 9.48.

What is claimed is:
1. A compound having the general formula

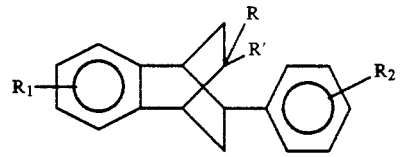

including pharmaceutically acceptable salts thereof, wherein

R and R' taken together with the carbon atom to which they are attached form a 5- to 7-membered nitrogen-containing ring

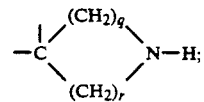

R$_1$ is hydrogen, halogen, alkyl, haloalkyl, cyano, hydroxy, alkoxy, aryl, arylalkoxy, arylalkyl, or fluorosubstituted alkyl;

R$_2$ is hydrogen, halogen, alkyl, alkoxy, aryloxy, arylalkoxy, arylalkyl, cyano, hydroxy, alkanoyloxy, —O—C(O)—NY$_1$Y$_2$, fluoro substituted alkoxy, fluoro substituted alkyl, (cycloalkyl)alkoxy, —NO$_2$, —NH$_3$Y$_4$, —S(O)$_m$alkyl, —S(O)$_m$aryl, —C(O)—Y$_5$ or —O—C—(O)—Y$_6$;

m is 0, 1 or 2;

q and r are independently 0, 1, 2 or 3, with the proviso that one of q and r must be other than zero;

Y$_1$ and Y$_2$ are each independently hydrogen, alkyl, aryl or heteroaryl, or Y$_1$ and Y$_2$ together with the nitrogen atom to which they are attached are pyrrolidinyl, piperidinyl or morpholinyl;

Y$_3$ and Y$_4$ are each independently hydrogen, alkyl, alkanoyl, arylcarbonyl, heteroarylcarbonyl, or —C(O)—NY$_1$Y$_2$;

Y$_5$ is hydroxy, alkoxy, aryloxy, amino, alkylamino or dialkylamino; and,

Y$_6$ is alkyl, alkoxy or aryloxy.

2. A compound of claim 1 having the name (1R*,2R*,4S*,9S*)-1,2,3,4-Tetrahydro-9-(4-methoxyphenyl)spiro[1,4-ethanonaphthalene-2,3'-pyrrolidine], monohydrochloride.

3. A compound having the name (1R*,2S*,4R*)-1,2,3,4-Tetrahydro-9-(4-methoxyphenyl)spiro-[1,4-ethenonaphthalene-2,3'-pyrrolidine], monohydrochloride.

4. A compound of claim 1 having the name (1R*,2S*,4S*,9S*)-1,2,3,4-Tetrahydro-9-(4-methoxyphenyl)spiro[1,4-ethanonaphthalene-2,3'-pyrrolidine], monohydrochloride.

5. A method of treating a cardiovascular disorder, comprising the step of administering a compound of claim 1 in an amount effective therefor to a subject in need thereof.

* * * * *